(12) United States Patent
Dauner et al.

(10) Patent No.: US 6,458,148 B1
(45) Date of Patent: Oct. 1, 2002

(54) STRAND-LIKE IMPLANT OF RESORBABLE POLYMER MATERIAL, PROCESS FOR ITS PRODUCTION AND USE IN SURGERY

(75) Inventors: Martin Dauner, Esslingen; Helmut Goldmann, Tuttlingen; Helmut Hierlemann, Goeppingen; Heinrich Planck, Nuertingen, all of (DE)

(73) Assignee: Aesculag AG & Co. KG (DE)

( * ) Notice: Subject to any disclaimer, the term of this patent is extended or adjusted under 35 U.S.C. 154(b) by 0 days.

(21) Appl. No.: 09/531,841

(22) Filed: Mar. 20, 2000

(30) Foreign Application Priority Data

Mar. 19, 1999 (DE) .......................... 199 12 360

(51) Int. Cl.[7] ............... A61F 2/02; A61K 9/22
(52) U.S. Cl. ............. 606/228; 623/23.58; 623/13.18
(58) Field of Search .................. 623/23.58, 23.75, 623/13.18, 13.19, 13.2; 606/228

(56) References Cited

U.S. PATENT DOCUMENTS

| | | | | |
|---|---|---|---|---|
| 4,347,234 A | * | 8/1982 | Wahlig et al. ............... 624/15 |
| 4,792,336 A | * | 12/1988 | Hlavacek et al. ......... 623/13.18 |
| 5,007,939 A | | 4/1991 | Decommune et al. |
| 5,102,983 A | * | 4/1992 | Kennedy ...................... 528/354 |
| 5,147,400 A | * | 9/1992 | Kaplan et al. ............. 623/13.18 |
| 5,217,495 A | * | 6/1993 | Kaplan et al. ............. 623/13.18 |
| 5,383,931 A | | 1/1995 | Hehli et al. .................... 623/16 |
| 5,425,766 A | | 6/1995 | Bowald ........................ 623/13 |
| 5,425,984 A | | 6/1995 | Kennedy et al. |
| 5,569,250 A | * | 10/1996 | Sarver et al. ................... 606/69 |
| 5,578,046 A | | 11/1996 | Liu et al. |
| 5,674,286 A | | 10/1997 | D'Allesio et al. |
| 6,045,571 A | * | 4/2000 | Hill et al. .................... 606/228 |
| 6,165,217 A | * | 12/2000 | Hayes ....................... 623/11.11 |
| 6,171,338 B1 | * | 1/2001 | Talja et al. ................. 623/11.11 |
| 6,183,499 B1 | * | 2/2001 | Fischer et al. ................ 606/228 |
| 6,241,771 B1 | * | 6/2001 | Gresser et al. ............. 623/17.16 |

FOREIGN PATENT DOCUMENTS

| | | |
|---|---|---|
| DE | 2257334 | 5/1973 |
| DE | 2849785 | 5/1979 |
| DE | 3701175 | 8/1988 |
| DE | 3801426 | 8/1989 |
| DE | 3830005 | 11/1989 |
| DE | 3830421 | 3/1990 |
| DE | 4018371 | 12/1990 |
| DE | 4012602 | 10/1991 |
| DE | 19521642 | 12/1996 |
| DE | 19613730 | 10/1997 |
| DE | 19721876 | 11/1998 |
| EP | 0241254 | 4/1987 |
| EP | 0241252 | 10/1987 |
| EP | 0272902 | 12/1987 |
| EP | 0429164 | 7/1990 |
| EP | 0625356 | 3/1991 |
| EP | 0452807 | 4/1991 |
| EP | 0677297 | 9/1994 |
| WO | 9820190 | 5/1998 |

\* cited by examiner

*Primary Examiner*—Corrine McDermott
*Assistant Examiner*—Suzette J. Jackson

(57) ABSTRACT

A strand-like implant of resorbable polymer material is substantially formed as a random copolymer of L-lactide and glycolide, which are present in a composition in a range of more than 80 mole % lactide and less than 20 mole % glycolide to 95 mole % lactide and 5 mole % glycolide, particularly in a ratio of 90:10, and has in the textile structure a tensile strength of more than 200 N/mm$^2$.

53 Claims, No Drawings

STRAND-LIKE IMPLANT OF RESORBABLE POLYMER MATERIAL, PROCESS FOR ITS PRODUCTION AND USE IN SURGERY

CROSS-REFERENCE TO RELATED APPLICATIONS

This application claims priority from German application No. 19912360.8, filed Mar. 19, 1999.

DESCRIPTION

The present invention relates to a strand-like implant of resorbable polymer material, a process for its production and its use in surgery.

Implants are frequently used in surgery for fixing and supporting, as well as for temporary or permanent replacement of damaged body parts. Examples are surgical suture threads, vascular prostheses, as well as artificial ligaments and fascicles.

Implants in the form of cords or bands have been developed, particularly for use in orthopedic surgery on humans and animals. They are e.g. used in the reconstruction or prosthetics in the area of the locomotor system, such as a cruciate knee ligament rupture.

However, when using non-resorbable materials, such as e.g. polytetrafluoro-ethylene, there are often persistent foreign body reactions and delayed infections caused by the implant.

Developments have therefore been directed towards partly or completely body-resorbable implant materials. Reference is made in this connection to the implant cord made from polydioxanone disclosed in the Ethicon German patent DE-C2 4012602. EP-B1-0 241 252 describes a lactide/glycolide polymer, which is end-masked with dodecanol.

The cords or bands known from the prior art suffer from a number of disadvantages. Thus, some resorbable materials have an accelerated resorption and therefore lead to an excessively rapid strength reduction, which impedes the result of the healing. High stiffness levels of the cords leads to a poor knotting behaviour and risks of an imprecise positioning in the operating field. In addition, the rough surfaces of the cords are prejudicial to the pull-through behaviour and can damage surrounding body tissue. The problem of the invention is to provide a strand-like implant of a resorbable polymer, which has good mechanical characteristics combined with a good decomposition and resorption behaviour in vivo, which is easy and inexpensive to manufacture and which can also be easily and reliably used for surgical implantations.

This problem is solved by a strand-like implant of resorbable polymer material, which is essentially formed as a random copolymer of L-lactide and glycolide, in which the L-lactide and glycolide are present in a composition in the range of more than 80 mole % lactide and less than 20 mole % glycolide to 95 mole % lactide and 5 mole % glycolide, particularly in a ratio of 90:10, which has in the textile structure a tensile strength of more than 200 N/mm$^2$. Preference is given to a tensile strength of more than 250 N/mm$^2$ based on the total cross-section of the implant. As the structure generally only contains approximately 50 to 70% polymer material in the cross-section, the tensile strength based on the polymer of the structure is correspondingly higher. The tensile strength can be in the range 400 to 500 N/mm$^2$.

Advantageously the implant according to the invention is characterized by an elongation at break of less than 30%, particularly less than 20%. Preferably an implant strand according to the invention has an elongation at break of 15 to 20%. Preference is given according to the invention to implants having a limited extension combined with a high breaking force. The implant is also preferably characterized in that the polymer material is not end-masked in its molecular structure. As a result of the correlation of the structure and polymer characteristics particularly advantageous physical and chemical properties are obtained for the implant according to the invention. It in particular exclusively comprises lactide and glycolide components, an end-masking being unnecessary.

Advantageously for an application of the invention the average molecular weight of the resorbable polymer material is at least 50,000 Dalton. According to the invention the average molecular weight can be 100,000 to 500,000 and in particular 200,000 Dalton. Such an average molecular weight value can also be obtained by mixing polymer fractions having different molecular weights.

The setting of the desired molecular weight can take place during the polymerization process according to procedures known to the experts. With a long-lasting polymerization reaction the viscosity of the polymer product obtained can decrease again through the formation of a balanced reaction. A checking of the degree of polymerization and the molecular weight obtained can take place by sampling and measuring the viscosity. Viscosity measurements take place in chloroform at 25° C. in a 0.1% solution.

Advantageously the polymer material in the finished implant has a residual monomer content of less than 1 and in particular less than 0.5 wt. %, based on the total polymer. The monomer present can be a lactide monomer, glycolide monomer or a mixture of both. The low content of unreacted monomer can influence the decomposition behaviour of the resorbable polymer in a manner advantageous for the invention. By controlling the unpolymerized monomer content it is possible to influence the decomposition profile. The setting of the residual monomer content can take place during the polymerization process using procedures known to the experts.

According to the invention, the inherent viscosity of the polymer material in the finished implant can be in the range 0.7 to 1.3 dl/g. For example, preferably the inherent viscosity of a raw fibre spun from the polymer material according to the invention can be 0.9 to 1.2 dl/g. Preferably the inherent viscosity of a textile strand produced from the polymer material according to the invention can be 0.9 to 1.1 dl/g.

The chemical composition and molecular structure of the copolymers according to the invention, combined with the structure of the implant, have an advantageous action on the characteristics of products produced therefrom. Examples thereof are favourable mechanical characteristics such as good flexibility, e.g. low flexural rigidity, good modulus behaviour and good knotting characteristics, such as are desired in particular for medical applications, e.g. in surgical implants.

The decomposition of the implant according to the invention takes place in the body of an animal or a human in which it was implanted during surgery as a result of hydrolysis processes. Under physiological conditions tissue and body fluids participate in the reaction. The decomposition process can take place hydrolytically and/or enzymatically, the polymer chain being split into smaller and more readily soluble fragments. The decomposition products are conveyed away by the metabolic system and are discharged from the organism in the same way as other metabolic waste materials. For a good compatibility of the resorbable implant material in the patient, it is important that during the decomposition process no harmful metabolites form or are enriched. The unmasked lactide-glycolide polymers according to the invention are in particular characterized in that no toxic decomposition products are formed during their decomposition in vivo. Experimental investigations on resorbable polymer strand-like implants according to the invention have revealed that decomposition in vitro takes place in roughly the same way as decomposition in vivo.

The implant according to the invention can be advantageously characterized in that the half-life period of its strength in vitro and in vivo is 8 to 16 and in particular 10 to 14 weeks. This means that at the end of 10 to 14 weeks the remaining strength still has half the original strength value. Within this time period the natural endogenous tissue can re-form to such an extent that it can take over the strength functions again. Thus, there is gradually a sliding taking over of the function fulfilled by the implant by the natural body tissue until finally the implant material is completely resorbed and removed from the body. The implant according to the invention is preferably characterized in that its in vivo resorption time is 6 to 18 months. Advantageously the resorption time of the implant is in particular 9 to 12 months.

The copolymer of L-lactide and glycolide to be used for the implant strand according to the invention can be obtained by random copolymerization of the starting monomers. To the monomer mixture can be added a suitable catalyst, e.g. tin octoate, in the conventionally necessary quantity. The reaction is performed as melt polymerization at temperatures above 150° C. in a suitable reactor, which is heatable and provided with a stirrer. In particular said polymerization reactor is designed in such a way that the resulting high viscosity melts are homogenized, the necessary temperature ranges can be maintained and the crude polymer can be substantially completely drained off from the reactor.

The lactide-glycolide copolymers can be extruded to filaments by conventional melt spinning processes. Melt spinning advantageously takes place at temperatures below 210° C., particularly temperatures in the range 160 to 200° C.

Advantageously the copolymer is extruded with an inherent viscosity of 1.2 to 2.3 dl/g, particularly 1.4 to 2.0 dl/g.

In order to obtain the necessary mechanical characteristics, the extruded filament can be stretched for orienting the molecular chains. The strengthened spinning filament can either be stretched directly or after winding up in a separate step in accordance with methods known to the experts.

For durably maintaining the orientation, mechanical characteristics and dimensional stability of the filaments of the finished implant, the stretched polymer material can be fixed by annealing. Fixing takes place at temperatures in the range between 50 and 150° C., preferably 70 and 130° C. The thermosetting process lasts between 1 and 72 hours. Annealing can take place with and without shrinking of the filament. In particularly preferred manner stretching and thermosetting are carried out directly following extrusion, particularly in a combined process. Advantageously for this purpose use is made of a corresponding apparatus of appropriate, combined devices. In a preferred embodiment of the invention monofilament or multifilament products of the copolymer can be exposed to a temperature of 50 to 150° C., with or without shrinkage, for a period of 20 to 50 hours in order to obtain dimensional stability.

In an embodiment of the process according to the invention the copolymer can be spun from the melt to filaments, which are stretched and annealed at 80 to 120° C. with a stretch ratio of 1:2 to 1:10.

Filament yarns from the resorbable polymer material according to the invention can be processed to strand-like implants using textile procedures known to the experts. In an embodiment of the invention the implant can be formed as a flat band.

In another embodiment of the invention the implant can be formed as a cord with a substantially round cross-section.

In a further embodiment of the invention the implant can be formed in a tube or a flat tube.

In a preferred embodiment the implant according to the invention can be characterized in that it is constructed with a composite structure of the core-jacket type.

Advantageously with the implant according to the invention the core can be formed by a yarn. In a preferred embodiment the core is formed from several yarns. According to the invention such a yarn can be formed from 3 to 300 single filaments, particularly 7 to 200 single filaments.

In another embodiment the implant according to the invention can be constructed in sewing or suture thread form.

The production of the yarns to be used for the core of the implant according to the invention can take place according to known yarn production processes. Advantageously the fibres in the yarn can have a slight twist. According to the invention the yarn is preferably folded, plied and/or twisted.

In the implant according to the invention the single fibres can have a thickness of more than 1 to 100 $\mu$m, particularly 10 to 20 $\mu$m, the latter corresponding to a fibre thickness of 1 to 4 dtex.

According to a further development, in the implant according to the invention single fibres of different thicknesses can be present in a composite structure. In particular, fibres in the inner area of the implant structure can be thicker than fibres in the outer area of the implant structure.

In a special embodiment of the invention it is possible to introduce so-called stationary threads into the implant composite structure.

Advantageously in an embodiment of the composite structure the polymer materials of individual textile components have similar physical and mechanical characteristics and a similar resorption behaviour. This permits a very uniform absorption and distribution of the forces which occur following the insertion of the implant in the patient. A very uniform resorption leads to a uniform strength decrease of the implant according to the invention, so that now weak points arise in the partly resorbed implant, which could disadvantageously affect the course of healing.

In another embodiment of the composite structure in which there is a selective decomposition of certain partial structures, the polymer materials of individual textile components can have a different resorption behaviour. Independently thereof the implant according to the invention comprises completely resorbable constituents.

As mentioned hereinbefore, the characteristics and in particular the mechanical characteristics of the strand-like implants can be favourably influenced by a suitable combination of chemical composition and structural design of the implants. For high tensile strength and low elongation at break preference is given to structures in which a very large number of fibres or yarns assume a minimum angle to the longitudinal direction of the strand-like implant and not only on average, but also at individual points, which can be potential break points if they are subject to pronounced bending.

In an embodiment of the strand-like implant according to the invention, it can be constructed as a woven textile structure. The warp threads assume a supporting function and are important for a high strength.

In another embodiment of the invention the strand-like implant can be constructed as a braided structure. With particular advantage the strand structure according to the invention can be constructed as a spiral braid. Preference is given to the use of a spiral braid with a small braiding angle of 5 to 30° (angular degrees) and 10 to 40, preferably 25 to 35, overlaps per French inch (27 mm).

The braided structure plays a part for the level of the breaking strength of the strand structure. If the braiding angle is excessive, the strand-like products have a low breaking force. The bonding of the threads in the textile structure is also important. Preferably in the case of a tubular braid there are 2 over 2 threads, but good values are also obtained with 1 over 1 thread, but an excessively loose structure results from weaves with 3 over 3 threads.

In an embodiment of a braided structure for the implant according to the invention it is possible to place a braid round a core. The core material can, as a function of the desired characteristics, be a textile structure of one yarn, several yarns or single filaments, in the manner described hereinbefore.

Advantageously the strand-like implants according to the invention are characterized by a low flexural rigidity, which facilitates handling in the case of medical applications and improves the knotting behaviour. The characteristics of the materials to be used for the core and jacket can be selected in such a way that an optimum composite structure is obtained. In addition, the textile methods for forming the core and jacket can be so selected that an optimum composite structure is obtained. Advantageously the textile structural methods for the core and jacket are so matched to one another that essentially the same behavioural characteristics, e.g. extension, occur for both core and jacket. With an unequal behaviour of the core and jacket, in the case of stressing there can be an excessive loading of the weaker component with the risk of premature failure. Thus, e.g. in an embodiment with a plied core and braided jacket the core can be relatively thick, so that it can carry virtually the entire load. In implants in the form of a cord with a substantially round cross-section, there can be two braided structures with a good cohesion of core and jacket. The implant according to the invention can also be constructed as a three-dimensional braided structure, in which the path of the threads not only takes place in a single plane or circumferential surface, but in all three dimensions, i.e. through the entire braid.

In a preferred embodiment of a braided, strand-like implant in the case of a braid in the core-jacket structure, the braiding can pass into the core. Such an interlacing increases the union between core and jacket in an advantageous manner. Interlacing can take place in such a way that the jacket braid passes through the core, so that the latter is no longer recognizable as a separate component. This gives a three-dimensional or 3D braid.

In another embodiment of the invention the implant can be constructed as a tubular braid with stationary threads. The stationary threads advantageously contribute to the strength and the mechanical characteristics.

In yet another embodiment of the invention the implant can be in the form of a knitted structure. Knitwear is advantageously used for tubular implants.

In the case of implants which, according to the invention, are constructed as composite structures, the union is preferably formed by textile joining methods. Thus, for example, as stated hereinbefore, in the case of braided implants the core and jacket threads can be braided together.

A process according to the invention for the production of a strand-like implant is characterized in that the resorbable polymer material, which is essentially formed as a random copolymer of L-lactide and glycolide, in which L-lactide and glycolide are present in a composition in the range of more than 80 mole % lactide and less than 20 mole % glycolide to 95 mole % lactide and 5 mole % glycolide, particularly in a ratio of 90:10, in the form of fibres is shaped in accordance with textile processing methods to a strand-like textile structure, in which the strand has a tensile strength of more than 200 N/mm$^2$, particularly more than 250 N/mm$^2$, based on the total cross-section of the braid.

Processes for the production of the polymer material according to the invention have been given hereinbefore. The copolymer is preferably spun from the melt to filaments, which at 80 to 120° C. are stretched and annealed with a stretch ratio of 1:2 to 1:10.

The polymers and the medical products produced therefrom in accordance with the present invention may be dyed or undyed. For resorbable medical products, it is possible to use for dyeing purposes dyes authorized by the U.S. Food and Drug Administration (FDA), such as e.g. D+C green No. 6, D+C violet No. 2, etc.

Implant strands according to the invention can be processed in accordance with conventional methods to implant material suitable for surgical applications, e.g. cut to suitable lengths. In order to prevent unravelling of the textile structure at the end of the strand, the ends of the implant strands can be secured in an appropriate manner. For example, the ends can be melted, sewn, bonded or ultrasonically welded. In an embodiment, at one or both ends of the strand-like implant can be provided a surgical aid such as a surgical suture needle or a pull-through device.

The desired characteristics of the implant according to the invention can be obtained in advantageous manner from the combination of the characteristics of the resorbable copolymer material and the textile design of the strand-like structure. During histological investigations there is no irritation to the tissue in the case of implants of the inventive strand in an animal test.

For use in medicine the polymer material according to the invention is in particular appropriately sterilized. An appropriate sterilization process can be chosen from conventional physical or chemical methods for inactivating microorganisms or a combination of such methods. One possible sterilization method comprises γ radiation treatment. Preferably the polymer material according to the invention is sterilized for medical products using ethylene oxide.

Advantageously the surgical implant material produced according to the invention can be appropriately cut to size and packed in sterile, appropriate ready-to-use form. In a preferred embodiment the inventive strands can be in an appropriate form for special application with surgical aids, such as transosteal pull-through devices.

Due to the hydrolytic decomposability of the inventive polymer material when the medical products are stored they must be protected against moisture and elevated temperatures, so that the strength characteristics are maintained fully up to the time of use. Advantageously, medical strands produced according to the invention are dried in the ready-to-use state and are appropriately packed. Advantageously this can take place in a moisture-proof pack, particularly a pack made from a moisture-impermeable film material, preferably a vacuum pack. In addition, a cool, dry storage location must be chosen.

Uses for the strand-like implant according to the invention are replacement transplants, prostheses, as well as augmentation transplants and grafting, particularly relative to the locomotor system of humans or animals. Examples for such surgical applications are treatment to damage on fascicles, ligaments or bonds resulting from injury or disease. Such implants can make the mobility of the patient much greater. Typical uses for the inventive implant are e.g. augmentation of the cruciate knee ligament, fixations to the bone and the fastening of soft tissue.

The implanted polymer material can absorb the forces exerted when the patient moves and keeps same away from the injured body structure. Thus, said area can heal in unstressed manner, whereas the resorbable polymer is gradually decomposed or degraded and returns the function to the natural structure. This permits an early mobilization of the patient following surgery, which avoids the impairment of the locomotor system and well-being due to postoperative immobilization.

Further features and details of the invention can be gathered from the following description of preferred embodiments in the form of examples. The individual features can be implemented singly or in combination with one another. The examples, which merely serve to illustrate the present invention, in no way restrict the latter.

EXAMPLE 1

Polymerization

A 10 liter double jacket reactor with paddle stirrer, stirrer motor and gas inlet is filled with 5400 g (37.5 mole) of L-lactide and 600 g (5.17 mole) of glycolide. After adding 1.2 g (0.0029 mole) of tin octoate (2-ethyl hexanoic acid-tin(II)-salt) dissolved in diethyl ether the reactor is sealed, evacuated and the mixture heated accompanied by stirring to 80° C. After 1 to 2 hours the reactor is placed under a pressure of 1 to 2 bar with argon, the temperature is raised to 200° C. and the reaction mixture is left under stirring for approximately 2 to 3 hours. The reaction material is then drained off and granulated.

The melting point of the granulated polymer is 152° C. (±2° C.) and the glass transition temperature is 51° C. (±2° C.). The inherent viscosity is 1.6±0.2 dl/g (0.1% solution in chloroform).

Extrusion and Stretching

The dried polymer (residual moisture content <0.01%) is extruded by means of a screw-type extruder, under a dry nitrogen stream, to a thread strand comprising 20 or 40 filaments. The pressure upstream of the spinning pump is 50 bar, the pressure between the spinning pump and the die is 100 to 200 bar, as a function of the starting viscosity of the polymer, the strainer and the throughput at the spinning pump. The spinning plate temperature is kept at 190° C. The thread strand is received by a take-up spool at a speed of 500 to 1000 m/min.

The thus obtained multifilament strand is oriented by a factor of 2 to 5 by stretching over a rail. The factor is dependent on the unwinding speed of the take-up spool. The tensile strength of the multifilament yarn after said heat treatment is 40 to 45 cN/tex. The titre of the yarn with 20 filaments is in the range 40 to 60 dtex and that with 40 filaments 80 to 120 dtex. The inherent viscosity is 1.1 dl/g (0.1% solution in chloroform).

Strand Structure

For producing a cord with a diameter of 2.0 mm the following braiding parameters were set and in connection with the titre details it must be borne in mind that these are plied core and jacket structures.

Thermal Aftertreatment (Post Treatment Process)

In order to improve the degradation behaviour of the cord, i.e. the half-life periods of the mechanical decomposition, it is necessary to significantly reduce the monomer content in the polymer matrix in a thermal aftertreatment process.

The finished strand structure is placed on a cylindrical steel roller under a tension of 10 N and aftertreated for 40 hours at 90° C. and a vacuum of <1 mbar. Following the posttreatment process the measured lactide monomer content is under 0.3%.

EXAMPLE 2

Tubular Braid Comprising Core and Jacket

| | |
|---|---|
| Core: | 20 bobbins × 750 dtex |
| Jacket: | 24 bobbins × 232 dtex |
| Braids/inch: | Jacket: 60, Core: plied |
| Titre: | 2276 tex |
| Diameter: | .04 mm |
| Max tensile strength: | 713 N |
| Breaking strength: | 226 N/mm$^2$ |
| Elongation at max tensile strength: | 18.8% |
| Half-life period in vitro: | approx. 77 days |

EXAMPLE 3

Tubular Braid, Jacket Braid

| | |
|---|---|
| Core: | |
| Jacket: | 24 bobbins × 840 dtex |
| Braids/inch: | Jacket: 8 |
| Titre: | 2142 tex |
| Diameter: | 1.85 mm |
| Max tensile strength: | 680 N |
| Breaking strength: | 225 N/mm$^2$ |
| Elongation at max tensile strength: | 19.5% |
| Half-life period in vitro: | approx. 80 days |

EXAMPLE 4

Spiral Braid

| | |
|---|---|
| Core: | 9 bobbins × 350 dtex |
| Jacket: | 20 bobbins in 1050 dtex |
| Braids/inch: | Jacket: 15, Core: 26 |
| Titre: | 2539 tex |
| Diameter: | 2.22 mm |
| Max tensile strength: | 660 N |
| Breaking strength: | 205 N/mm$^2$ |
| Elongation at max tensile strength: | 17.3% |
| Half-life period in vitro: | approx. 85 days |

EXAMPLE 5

Tubular Braid

| | |
|---|---|
| Core: | 8 bobbins × 1050 dtex |
| Jacket: | 16 bobbins in 897 dtex |
| Braids/inch: | Jacket: 24, Core: 16 |
| Titre: | 2402 tex |
| Diameter: | 1.98 mm |
| Max tensile strength: | 731 N |
| Breaking strength: | 232 N/mm² |
| Elongation at max tensile strength: | 16.9% |
| Half-life period in vitro: | approx. 80 days |

What is claimed is:

1. Strand-like implant of resorbable polymer material, which is essentially formed as a random copolymer of L-lactide and glycolide, in which L-lactide and glycolide are present in a composition in the range of from more than 80 mole % lactide up to 95 mole % lactide and from less than 20 mole % glycolide down to 5 mole % glycolide, wherein the molecular structure of said polymer material is not end-masked or end-capped, and wherein said implant, in a textile structure made of fiber yarn, has a tensile strength of more than 200 N/mm².

2. Implant according to claim 1, wherein the elongation at break is less than 30%.

3. Implant according to claim 2, wherein the elongation at break is less than 20%.

4. Implant according to claim 1, wherein the polymer material of the finished implant has a residual monomer content of less than 1 wt. %, based on the total polymer.

5. Implant according to claim 4, wherein the polymer material of the finished implant has a residual monomer content of less than 0.5 wt. % based on the total polymer.

6. Implant according to claim 1, wherein the inherent viscosity of the polymer material of the finished implant is 0.7 to 1.3 dl/g.

7. Implant according to claim 5, wherein the inherent viscosity of the polymer material of the finished implant is 0.9 to 1.2 dl/g.

8. Implant according to claim 1, wherein the half-life period of the implant's strength in vitro and in vivo is 8 to 16 weeks.

9. Implant according to claim 8, wherein the half-life period of the implant's strength in vitro and in vivo is 10 to 14 weeks.

10. Implant according to claim 1, wherein the implant has an in vivo resorption time of 6 to 18 months.

11. Implant according to claim 10, wherein the implant has an in vivo resorption time of 9 to 12 months.

12. Implant according to claim 1, wherein the implant is bending-slack.

13. Implant according to claim 1, wherein the implant is constructed in the form of a flat band.

14. Implant according to claim 1, wherein the implant is constructed in the form of a cord with a substantially round cross-section.

15. Implant according to claim 1, wherein the implant is constructed in the form of a tube or a flat tube.

16. Implant according to claim 1, wherein the implant is constructed as a composite structure of the core/jacket type.

17. Implant according to claim 12, wherein the core is formed by a yarn.

18. Implant according to claim 12, wherein the core is formed from several yarns.

19. Implant according to claim 1, wherein the implant is constructed as a suture thread.

20. Implant according to claim 1, wherein said fiber yarn is formed from 3 to 300 single filaments.

21. Implant according to claim 20, wherein said fiber yarn is formed from 7 to 200 single filaments.

22. Implant according to claim 1, wherein said fiber yarn is folded, plied and/or twisted.

23. Implant according to claim 1, wherein a single fibre of said implant has a thickness of 1 to 100 μm.

24. Implant according to claim 23, wherein a single fibre of said implant has a thickness of 10 to 20 μm.

25. Implant according to claim 1, wherein single fibres of different thicknesses are present in a composite structure.

26. Implant according to claim 25, wherein fibres in the inner area are thicker than in the other area.

27. Implant according to claim 1, wherein in a composite structure the polymer materials of individual textile components have similar physical and mechanical characteristics and a similar resorption behaviour.

28. Implant according to claim 1, wherein in a composite structure the polymer materials of individual textile components have a different resorption behaviour.

29. Implant according to claim 1, wherein the implant is constructed as a woven structure.

30. Implant according to claim 29, wherein said woven structure comprises warp threads in the longitudinal direction.

31. Implant according to claim 1, wherein the implant is constructed as a braided structure.

32. Implant according to claim 1, wherein the implant is constructed as a spiral braid.

33. Implant according to claim 1, wherein the implant is constructed as a spiral braid with a small braiding angle of 5 to 30° (angular degrees) and 10 to 40 overlaps per French inch (27 mm).

34. Implant according to claim 33, wherein said spiral braid is with 25 to 30 overlaps per French inch (27 mm).

35. Implant according to claim 1, wherein the implant is constructed as a tubular braid with stationary threads.

36. Implant according to claim 1, wherein the implant is constructed as a knitted structure.

37. Implant according to claim 1, wherein in composite structures the union is formed by textile joining methods.

38. Implant according to claim 1, wherein L-lactide and glycolide are present in a composition in a ratio of 90:10.

39. Process for the production of a strand-like implant, wherein resorbable polymer material is processed into fibres using textile processing methods so as to give a strand-like, textile structure made of fiber yarn, so that the implant has a tensile strength of more than 200 N/mm², wherein said resorbable polymer material is essentially formed from random copolymer of L-lactide and glycolide, in which L-lactide and glycolide are present in a composition in the range of from more than 80 mole % lactide up to 95 mole % lactide and from less than 20 mole % glycolide down to 5 mole % glycolide, and wherein the molecular structure of said polymer material is not end-masked or end-capped.

40. Process according to claim 39, wherein the copolymer is spun from a melt to filaments, which at 80 to 120° C. are stretched and annealed with a stretch ratio of 1:2 to 1:10.

41. Process according to claim 39, wherein the copolymer is spun from a melt, and wherein spinning of the melt takes place at temperatures below 210° C.

42. Process according to claim 41, wherein spinning of the melt takes place at temperatures in the range of 160 to 200° C.

43. Process according to claim 39, wherein the copolymer is extruded with an inherent viscosity of 1.2 to 2.3 dl/g.

44. Process according to claim 43, wherein the copolymer is extruded with an inherent viscosity of 1.4 to 2.0 dl/g.

45. Process according to claim 29, wherein L-lactide and glycolide are present in a composition in a ratio of 90:10.

46. Strand-like implant having a textile structure made of resorbable polymer material, wherein said polymer material is essentially formed as a random copolymer of L-lactide and glycolide, in which L-lactide and glycolide are present in a composition in the range of from more than 80 mole % lactide up to 95 mole % lactide and from less than 20 mole % glycolide down to 5 mole % glycolide, wherein the molecular structure of said polymer material is not end-masked or end-capped, and wherein said implant, in a textile structure made of fiber yarn, has a tensile strength of more than 200 N/mm$^2$, for use in surgery for prostheses and/or augmentation grafting.

47. Strand-like implant of resorbable polymer material, which is essentially formed as a random copolymer of L-lactide and glycolide, in which L-lactide and glycolide are present in a composition in the range of from more than 80 mole % lactide up to 95 mole % lactide and from less than 20 mole % glycolide down to 5 mole % glycolide, wherein the inherent viscosity of said polymer material of the finished implant is 0.7 to 1.3 dl/g, and wherein said implant, in a textile structure made of fiber yarn, has a tensile strength of more than 200 N/mm$^2$.

48. Strand-like implant of resorbable polymer material, which is essentially formed as a random copolymer of L-lactide and glycolide, in which L-lactide and glycolide are present in a composition in the range of from more than 80 mole % lactide up to 95 mole % lactide and from less than 20 mole % glycolide down to 5 mole % glycolide, wherein the half-life period of the implant's strength in vitro and in vivo is 8 to 16 weeks, and wherein said implant, in a textile structure made of fiber yarn, has a tensile strength of more than 200 N/mm$^2$.

49. Strand-like implant of resorbable polymer material, which is essentially formed as a random copolymer of L-lactide and glycolide, in which L-lactide and glycolide are present in a composition in the range of from more than 80 mole % lactide up to 95 mole % lactide and from less than 20 mole % glycolide down to 5 mole % glycolide, wherein said implant, in a textile structure made of fiber yarn, has a tensile strength of more than 200 N/mm$^2$, and wherein a single fibre of said implant has a thickness of 1 to 100 μm.

50. Strand-like implant of resorbable polymer material, which is essentially formed as a random copolymer of L-lactide and glycolide, in which L-lactide and glycolide are present in a composition in the range of from more than 80 mole % lactide up to 95 mole % lactide and from less than 20 mole % glycolide down to 5 mole % glycolide, wherein said implant, in a textile structure made of fiber yarn, has a tensile strength of more than 200 N/mm2, and wherein said implant is constructed as a spiral braid with a small braiding angle of 5 to 30° (angular degrees) and 10 to 40 overlaps per French inch (27 mm).

51. Process for the production of a strand-like implant, wherein resorbable polymer material is processed into fibres using textile processing methods so as to give a strand-like, textile structure made of fiber yarn, so that the implant has a tensile strength of more than 200 N/mm$^2$, wherein said resorbable polymer material is essentially formed from random copolymer of L-lactide and glycolide, in which L-lactide and glycolide are present in a composition in the range of from more than 80 mole % lactide up to 95 mole % lactide and from less than 20 mole % glycolide down to 5 mole % glycolide, wherein the molecular structure of said polymer material is not end-masked or end-capped, and wherein the copolymer is spun from a melt to filaments, which at 80 to 120° C. are stretched and annealed with a stretch ratio of 1:2 to 1:10.

52. Process for the production of a strand-like implant, wherein resorbable polymer material is processed into fibres using textile processing methods so as to give a strand-like, textile structure made of fiber yarn, so that the implant has a tensile strength of more than 200 N/mm$^2$, wherein said resorbable polymer material is essentially formed from random copolymer of L-lactide and glycolide, in which L-lactide and glycolide are present in a composition in the range of from more than 80 mole % lactide up to 95 mole % lactide and from less than 20 mole % glycolide down to 5 mole % glycolide, wherein the molecular structure of said polymer material is not end-masked or end-capped, wherein the copolymer is spun from a melt, and wherein spinning of the melt takes place at temperatures below 210° C.

53. Process for the production of a strand-like implant, wherein resorbable polymer material is processed into fibres using textile processing methods so as to give a strand-like, textile structure made of fiber yarn, so that the implant has a tensile strength of more than 200 N/mm$^2$, wherein said resorbable polymer material is essentially formed from random copolymer of L-lactide and glycolide, in which L-lactide and glycolide are present in a composition in the range of from more than 80 mole % lactide up to 95 mole % lactide and from less than 20 mole % glycolide down to 5 mole % glycolide, wherein the molecular structure of said polymer material is not end-masked or end-capped, and wherein said copolymer is extruded with an inherent viscosity of 1.2 to 2.3 dl/g.

* * * * *

UNITED STATES PATENT AND TRADEMARK OFFICE
CERTIFICATE OF CORRECTION

PATENT NO. : 6,458,148 B1
DATED : October 1, 2002
INVENTOR(S) : Dauner et al.

It is certified that error appears in the above-identified patent and that said Letters Patent is hereby corrected as shown below:

Title page,
Item [73], Assignee, "Aesculag" should read -- Aesculap --

Column 2,
Line 44, "fibre" should read -- fiber --

Column 4,
Lines 31, 33, 38, 40 and 41 "fibres" should read -- fibers --
Line 35, "fibre" should read -- fiber --

Column 5,
Line 1, "fibres" should read -- fibers --

Column 6,
Line 16, "fibres" should read -- fibers --

Column 9,
Line 38, "claim 5" should read -- claim 6 --
Lines 62 and 64, "claim 12" should read -- claim 16 --

Column 10,
Lines 7 and 9, "fibre" should read -- fiber --
Lines 11, 13 and 46, "fibres" should read -- fibers --

Column 11,
Line 3, "claim 29" should read -- claim 39 --
Line 45, "fibre" should read -- fiber --

UNITED STATES PATENT AND TRADEMARK OFFICE
CERTIFICATE OF CORRECTION

PATENT NO.   : 6,458,148 B1
DATED        : October 1, 2002
INVENTOR(S)  : Dauner et al.

It is certified that error appears in the above-identified patent and that said Letters Patent is hereby corrected as shown below:

<u>Column 12,</u>
Lines 7, 22 and 36, "fibres" should read -- fibers --

Signed and Sealed this

Eleventh Day of March, 2003

JAMES E. ROGAN
*Director of the United States Patent and Trademark Office*